(12) United States Patent
Takasu et al.

(10) Patent No.: US 7,737,235 B2
(45) Date of Patent: Jun. 15, 2010

(54) VINYL MONOMER AND POLYMER DERIVED FROM THE MONOMER, AND LIGHT EMITTING DEVICE USING THE POLYMER

(75) Inventors: Takako Takasu, Kanagawa (JP); Ryoji Nomura, Kanagawa (JP); Satoshi Seo, Kanagawa (JP)

(73) Assignee: Semiconductor Energy Laboratory Co., Ltd., Atsugi-shi, Kanagawa-ken (JP)

( * ) Notice: Subject to any disclaimer, the term of this patent is extended or adjusted under 35 U.S.C. 154(b) by 0 days.

(21) Appl. No.: 12/486,803

(22) Filed: Jun. 18, 2009

(65) Prior Publication Data

US 2009/0259008 A1 Oct. 15, 2009

Related U.S. Application Data

(62) Division of application No. 10/899,296, filed on Jul. 27, 2004, now Pat. No. 7,579,419.

(30) Foreign Application Priority Data

Jul. 28, 2003 (JP) ............................. 2003-280689

(51) Int. Cl.
*C08F 126/06* (2006.01)
(52) U.S. Cl. ..................... 526/256; 526/258; 526/266
(58) Field of Classification Search ................ 526/256, 526/258, 266
See application file for complete search history.

(56) References Cited

U.S. PATENT DOCUMENTS

| 3,294,763 A | 12/1966 | Hewett |
| 5,223,591 A | 6/1993 | Nyander |
| 6,730,450 B1 * | 5/2004 | Moffat et al. ............ 430/108.5 |
| 7,071,289 B2 * | 7/2006 | Sotzing ...................... 528/377 |

FOREIGN PATENT DOCUMENTS

| DE | 1 570 808 | 6/1970 |
| DE | 1 593 912 | 9/1970 |
| JP | 08-020614 | 1/1996 |
| JP | 2000-087027 | 3/2000 |

| WO | WO 90/11303 | 10/1990 |

OTHER PUBLICATIONS

Kim et al., Chemistry Letters vol. 33, No. 1 (2004).*
S.A. Carter et al.; "Polymeric anodes for improved polymer light-emitting diode performance"; *Applied Physics Letters* 70(16); pp. 2067-2069; 1997.
Y. Yang et al.; "Polyaniline as a transparent electrode for polymer light-emitting diodes: Lower operating voltage and higher efficiency"; *Applied Physics Letters* 64(10); pp. 1245-1247; 1994.
Kim et al., *New Conducting Polymers Based on Poly(3,4-ethylenedioxpyrrole): Synthesis, Characterization, and Properties*, Chemistry Letters, vol. 33, No. 1 (2004), p. 46-47.
Search Report (European Application No. 04747310.3) mailed Jul. 23, 2007, 3 pages.
Paul Anderson et al.; "Synthesis of 9,10-Dihydroanthracen-9,10-imines"; *J. Org. Chem.*, vol. 44, No. 9; pp. 1519-1533; 1979.
J.L. Brédas et al.; "Electronic and nonlinear optical properties of polyarylene vinylenes and related conjugated systems"; *SPIE vol. 971—Nonlinear Optical Properties of Organic Materials*; pp. 42-50; 1988.
International Search Report and Written Opinion (Application No. PCT/JP2004/009842) dated Sep. 21, 2004 (with partial translation).

* cited by examiner

*Primary Examiner*—Robert D. Harlan
(74) *Attorney, Agent, or Firm*—Fish & Richardson P.C.

(57) ABSTRACT

It is an object of the present invention to provide a polymer that is soluble in an organic solvent with a low polarity and has a high hole injecting property without adding a dopant for enhancing a hole injecting property. For that object, the present invention provides a vinyl monomer represented by the following general formula (1). In the formula, X represents any one of an oxygen atom (O) and a sulfur atom (S). Y represents any one of a hydrogen atom, an alkyl group, aryl group, a silyl group having an alkyl group or an aryl group as a substituent.

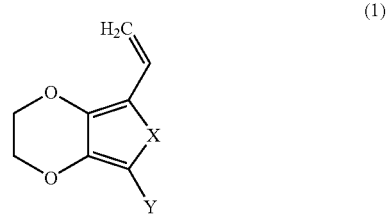

(1)

29 Claims, 4 Drawing Sheets

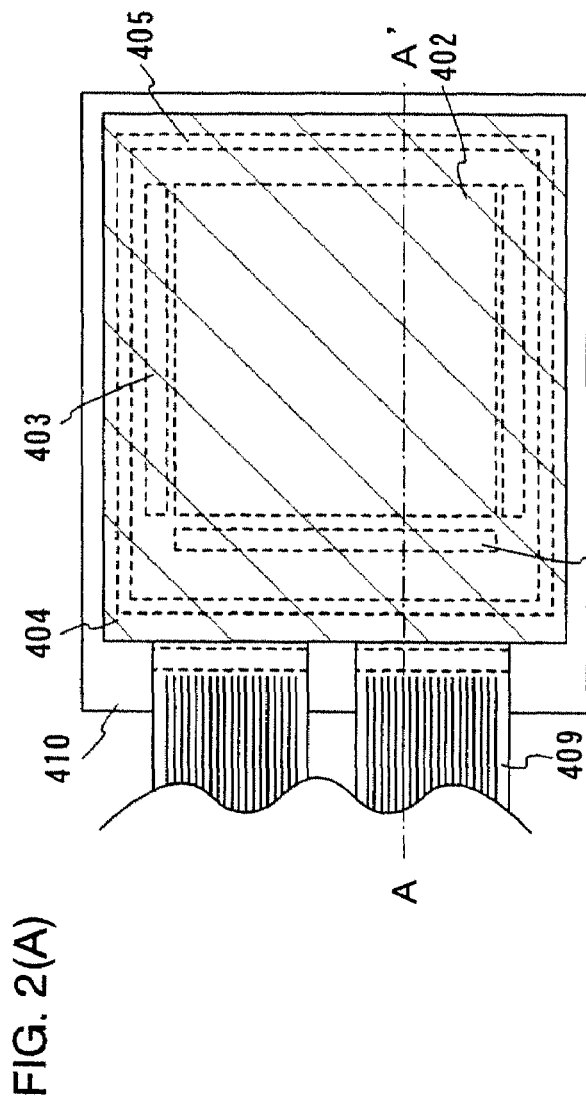
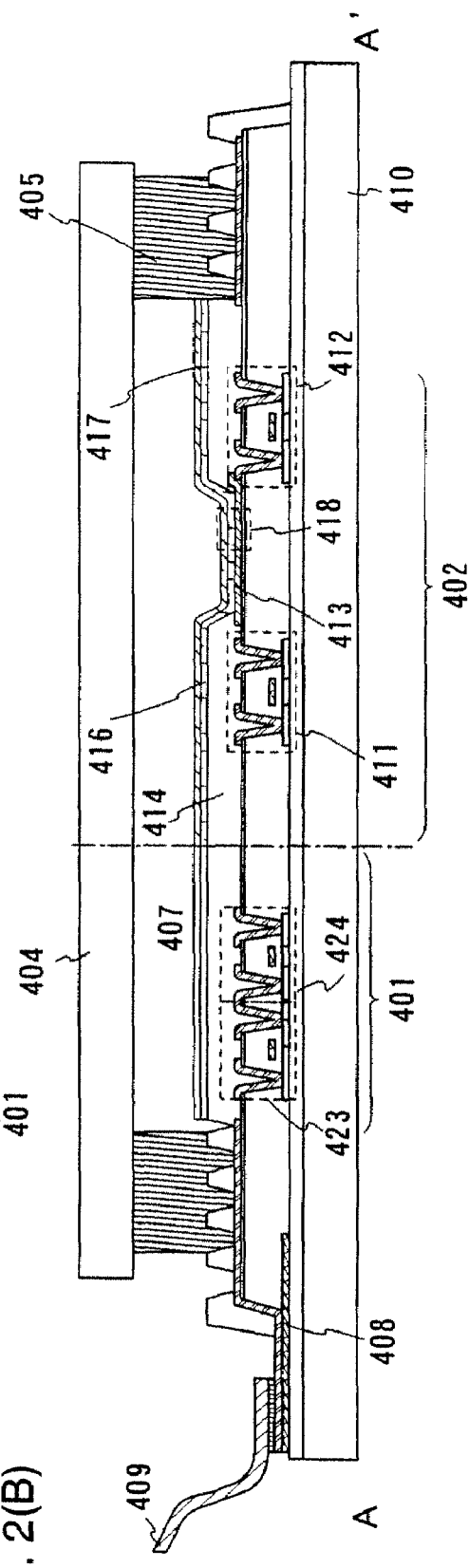

VINYL MONOMER AND POLYMER DERIVED FROM THE MONOMER, AND LIGHT EMITTING DEVICE USING THE POLYMER

CROSS-REFERENCE TO RELATED APPLICATIONS

This application is a divisional of U.S. application Ser. No. 10/899,296, filed Jul. 27, 2004, now allowed, which claims the benefit of a foreign priority application filed in Japan as Serial No. 2003-280689 on Jul. 28, 2003, both of which are incorporated by reference.

TECHNICAL FIELD

The present invention relates to a polymer that has a function of promoting hole injection, and to a vinyl monomer that is used as a material for synthesizing the polymer. In addition, the present invention relates to a light-emitting element using the polymer.

BACKGROUND ART

A display for displaying images is one of light-emitting elements necessary in modem life, which takes various configurations, such as so-called TV monitors, liquid crystal displays that have been developed rapidly in recent years, and EL (Electro Luminescence) displays that are expected to develop future, to meet requirements. Above all, an organic EL display has been most attracting attention as a next-generation flat panel display device.

In the light-emission mechanism of a light-emitting element composing an organic EL display, by locating a light-emitting layer composed of a composition that has a light-emitting property between electrodes and applying a current, an electron injected from a cathode and a hole injected from an anode are recombined in a luminescent center of the light-emitting layer to form a molecular exciton, and a photon emitted when the molecular exciton returns to the ground state is used. Therefore, injecting a hole and an electron into an organic thin film efficiently is one of requirements for manufacturing a high-efficiency light-emitting element.

In an operating condition of an electroluminescent element, typically, a current around 100 mA/cm$^2$ is injected into a basically high electric resistance organic thin film. In order to realize the high-density current injection like this, it is necessary to reduce a hole-injection barrier from an anode and an electron-injection barrier from a cathode as mush as possible. Namely, a metal that has a small work function must be used as the cathode while an electrode that has a large work function must be selected as the anode. As for the cathode, by selecting various metals or alloys, the work function can be controlled virtually at will. On the contrary, in a general light-emitting element, what happening now is that an anode is limited to a transparent conductive oxide since the anode is required to have transparency, and in consideration of stability, transparency, resistivity, and the like, it is inevitable that several oxide conductive films typified by indium-tin oxide (hereinafter, referred to as ITO) are selected at this time. The work function of an ITO film can be changed to be made larger by a background during deposition or surface treatment. However, the method like this has limitations. This blocks reducing the hole-injecting barrier.

As one of methods for reducing a hole-injection barrier from an ITO anode, it is known to insert a buffer layer on the ITO film. By optimizing the ionization potential of the buffer layer, the hole-injection barrier can be reduced. The buffer layer like this is referred to as a hole injecting layer. As representatives of ones that function as a hole injecting layer, conjugated polymers can be cited. As typical examples, conjugated polymers such as polyanilines (Non-Patent Reference 1) and polythiophene derivatives (Non-Patent Reference 2) are known. By using the material as a hole injecting layer, the hole-injection barrier is reduced, and holes are efficiently injected, so that a light-emitting element is improved in efficiency and life, and the driving voltage can also be reduced.

These polymer materials, in which a sufficient hole injecting property cannot be achieved by only the conjugated polymers, always need a dopant for enhancing a hole injecting property. As the dopant, strongly acidic materials such as poly (styryl sulfonic acid) and camphorsulfonic acid are often used. However, there is a possibility that these strongly acidic materials have harmful effects on a transistor for driving a light-emitting element, for example, in an active matrix display device. Further, these polymer materials generally dissolve only in water or a solvent with high polarity. Therefore, after a polymer solution manufactured by dissolving the conjugated polymer material described above in these solvents is applied to a substrate, it is necessary to remove the solvent with a high boiling point at a high temperature under reduced pressure. In this method, it is not always easy to remove the solvent, in particular, water, thus it is conceivable that degradation of an element is accelerated by remaining solvent.

Based on these technological back ground, a hole injecting polymer that needs no dopant for enhancing a hole injecting property and is soluble in an organic solvent with a low boiling point, that is, a low polarity.

Non-Patent Reference 1: Y. Yang, et al., Appl. Phys. Lett. 1994, 64, 1245-1247

Non-Patent Reference 2: S. A. Carter, et al., Appl. Phys. Lett. 1997, 70, 2067-2069

DISCLOSURE OF THE INVENTION

Problems to be Solved by the Invention

It is an object of the present invention to provide a polymer that is soluble in an organic solvent with a low polarity and has a high hole injecting property without adding a dopant for enhancing a hole injecting property.

Means for Solving the Problems

The present invention provides a polymer (polymer or copolymer) that has a function of promoting hole injection, and a vinyl monomer that can be used as a material for synthesizing the polymer.

The present invention provides vinyl monomers represented by the following general formulas or structure formulas (1) to (5).

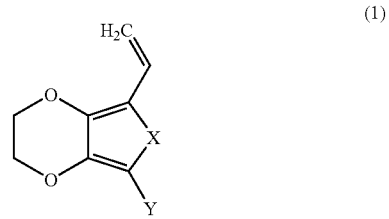

(In the formula, X represents any one of an oxygen atom (O) and a sulfur atom (S). Y represents any one of a hydrogen atom, an alkyl group, an aryl group, and a silyl group having an alkyl group or an aryl group as a substituent.)

(2)

(In the formula, Y represents any one of a hydrogen atom, an alkyl group, an aryl group, and a silyl group having an alkyl group or an aryl group as a substituent. Z represents any one of a hydrogen atom, an alkyl group, and an unsubstituted or substituted aryl group.)

(3)

(In the formula, X represents any one of an oxygen atom (O) and a sulfur atom (S). In the formula, Y represents any one of a hydrogen atom, an alkyl group, an aryl group, and a silyl group having an alkyl group or an aryl group as a substituent.)

(4)

(In the formula, Y represents any one of a hydrogen atom, an alkyl group, an aryl group, and a silyl group having an alkyl group or an aryl group as a substituent. Z represents any one of a hydrogen atom, an alkyl group, and an unsubstituted or substituted aryl group.)

(5)

The present invention provides polymers represented by the following general formulas or structure formulas (6) to (10).

(6)

(In the formula, X represents any one of an oxygen atom (O) and a sulfur atom (S). Y represents any one of a hydrogen atom, an alkyl group, an aryl group, and a silyl group having an alkyl group or an aryl group as a substituent. n is an integer of 2 or more.)

(7)

(In the formula, Y represents any one of a hydrogen atom, an alkyl group, an aryl group, and a silyl group having an alkyl group or an aryl group as a substituent. Z represents any one of a hydrogen atom, an alkyl group, and an unsubstituted or substituted aryl group. n is an integer of 2 or more.)

(8)

(In the formula, X represents any one of an oxygen atom (O) and a sulfur atom (S). Y represents any one of a hydrogen atom, an alkyl group, an aryl group, and a silyl group having an alkyl group or an aryl group as a substituent. n is an integer of 2 or more.)

(9)

(In the formula, Y represents any one of a hydrogen atom, an alkyl group, an aryl group, and a silyl group having an alkyl group or an aryl group as a substituent. Z represents any one of a hydrogen atom, an alkyl group, and an unsubstituted or substituted aryl group. n is an integer of 2 or more.)

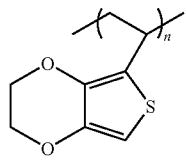

(10)

(In the formula, n is an integer of 2 or more.)

The present invention provides copolymers represented by the following general formulas or structure formulas (11) to (15).

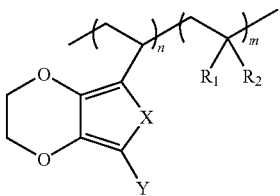

(11)

(In the formula, X represents any one of an oxygen atom (O) and a sulfur atom (S). Y represents any one of a hydrogen atom, an alkyl group, an aryl group, and a silyl group having an alkyl group or an aryl group as a substituent. $R_1$ represents a hydrogen atom or an alkyl group. $R_2$ represents any one of an unsubstituted or substituted aryl group, an ester group, a cyano group, an amide group, an alkoxy group, an oxycarbonylalkyl group, and a diarylamino group. n and m are individually an integer of 1 or more.)

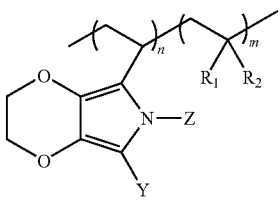

(12)

(In the formula, Y represents any one of a hydrogen atom, an alkyl group, an aryl group, and a silyl group having an alkyl group or an aryl group as a substituent. Z represents any one of a hydrogen atom, an alkyl group, and an unsubstituted or substituted aryl group. $R_1$ represents a hydrogen atom or an alkyl group. $R_2$ represents any one of an unsubstituted or substituted aryl group, an ester group, a cyano group, an amide group, an alkoxy group, an oxycarbonylalkyl group, and a diarylamino group. n and m are individually an integer of 1 or more.)

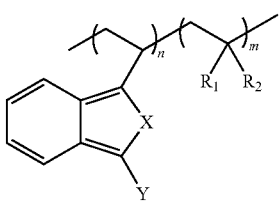

(13)

(In the formula, X represents any one of an oxygen atom (O) and a sulfur atom (S). Y represents any one of a hydrogen atom, an alkyl group, an aryl group, and a silyl group having an alkyl group or an aryl group as a substituent. $R_1$ represents a hydrogen atom or an alkyl group. $R_2$ represents any one of an unsubstituted or substituted aryl group, an ester group, a cyano group, an amide group, an alkoxy group, an oxycarbonylalkyl group, and a diarylamino group. n and m are individually an integer of 1 or more.)

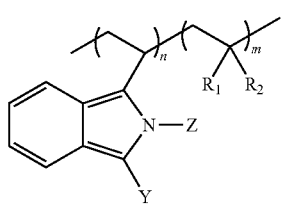

(14)

(In the formula, Y represents any one of a hydrogen atom, an alkyl group, an aryl group, and a silyl group having an alkyl group or an aryl group as a substituent. Z represents any one of a hydrogen atom, an alkyl group, and an unsubstituted or substituted aryl group. $R_1$ represents a hydrogen atom or an alkyl group. $R_2$ represents any one of an unsubstituted or substituted aryl group, an ester group, a cyano group, an amide group, an alkoxy group, an oxycarbonylalkyl group, and a diarylamino group. n and m are individually an integer of 1 or more.)

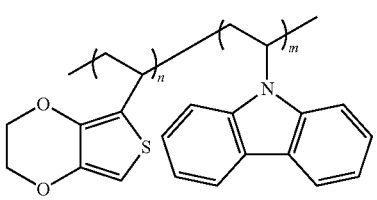

(15)

(n and m are individually an integer of 1 or more.)

In the vinyl monomers represented by the above general formulas or structure formulas (1) to (5), vinyl groups contributing polymerization, which are conjugated with an aromatic substituent such as thiophene or a furan skeleton, are active in polymerization. In addition, since a thiophene ring, a furan skeleton, and a pyrrole ring are hetero aromatic rings that have excess electrons, the vinyl groups have an improved electron density. Therefore, the vinyl monomers represented by the above general formulas or structure formulas (1) to (5) easily give polymers by radical polymerization or cation polymerization. Additionally, in the vinyl monomers represented by the above general formulas (1) to (4), the solubility is increased by making Y in the formula a substituent other than a hydrogen atom, for example, an alkyl group, an aryl group, or a silyl group having an alkyl group or an aryl group as a substituent.

Further, in the monomers described above, the ionization potential of the hetero ring is quite small due to an oxyethylene group introduced in a hetero ring of 5-membered ring or a directly condensed benzene ring. Therefore, the polymers and copolymers represented by the general formulas or structure formulas (6) to (15), which are synthesized by polymerizing the monomer, are superior in hole injecting property. In the case where Y in the formula is an aryl group, the hole injecting property is further improved. In addition, in the polymers represented by the general formulas or structure formulas (6) to (10), n is preferably an integer of 10 or more from the viewpoint of improvement in heat resistance. Further, in the copolymers represented by the general formulas or structure formulas (11) to (15), the sum of n and m is preferably an integer of 10 or more (however, n is an integer of 1 or more) from the viewpoint of improvement in heat resistance.

In particular, in the copolymer represented by the structure formula (15), the vinyl monomer represented by the structure formula (5) and vinyl carbazole that is a hole transporting material are copolymerized to show a more hole injecting property. Other than vinyl carbazole, a material that has aryl amine as a side chain can be used. For example, it is possible to cite a copolymer represented by the general formula (13), which is a material in which $R_1$ is a hydrogen atom, and $R_2$ is represented by any one of the following structure formulas (16), (17), (18), and (19).

(16)

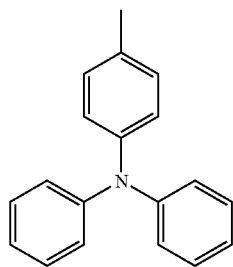

(17)

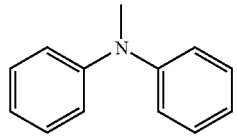

(18)

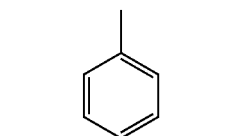

(19)

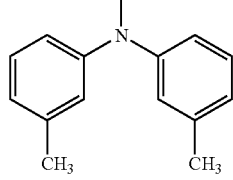

Another structure of the present invention is a light-emitting element that has the polymer or copolymer represented by any of the above general formulas or structure formulas (6) to (15).

More specifically, the structure is a light-emitting element using the polymer or copolymer represented by any of the above general formulas or structure formulas (6) to (15) as a hole injecting layer.

The polymers or copolymers represented by the above general formulas or structure formulas (6) to (15) are superior in hole injecting property. Therefore, it is unnecessary to add a strongly acidic dopant for enhancing a hole injecting property. In addition, the polymers or copolymers are soluble in an organic solvent with a low polarity (organic solvent with a low boiling point). Therefore, it is unnecessary to use water or the like as a solvent, which is generally believed to be a material that causes degradation of a light-emitting element.

Effect of the Invention

The present invention can provide a hole injecting material to which it is unnecessary to add a dopant for promoting a hole injecting property, and further provide a hole injecting material that is soluble in an organic solvent with a low polarity. Therefore, in a light-emitting element using a polymer or copolymer according to the present invention, degradation of the light-emitting element due to water can be suppressed. Further, in an active matrix EL display device using the light-emitting element, a defect in a transistor due to a strongly acidic dopant can be suppressed.

BRIEF DESCRIPTION OF DRAWINGS

FIG. 2 is a diagram for describing a light-emitting device using a layer comprising a polymer according to the present invention as a part.

EXPLANATION OF REFERENCE

11 substrate, 12 anode, 13 hole injecting material, 14 hole transporting material, 15 light-emitting layer, 16 electron transporting layer, 17 cathode, 401 source side driver circuit, 402 pixel portion, 403 gate side driver circuit, 404 sealing substrate, 405 sealing material, 407 space, 408 wiring, 409 FPC, 410 substrate, 423 n-channel TFT, 424 p-channel TFT, 411 switching TFT, 412 current controlling TFT, 413 electrode, 414 insulator, 416 layer, 417 electrode, 418 light-emitting element, 5501 frame body, 5502 support, 5503 display portion, 5511 main body, 5512 display portion, 5513 voice input, 5514 operation switches, 5515 battery, 5516 image receiving portion, 5521 main body, 5522 frame body, 5523 display portion, 5524 keyboard, 5531 main body, 5532 stylus, 5533 display portion, 5534 operation buttons, 5535 external interface, 5551 main body, 5552 display portion (A), 5553 eye piece, 5554 operation switches, 5555 display portion (B),

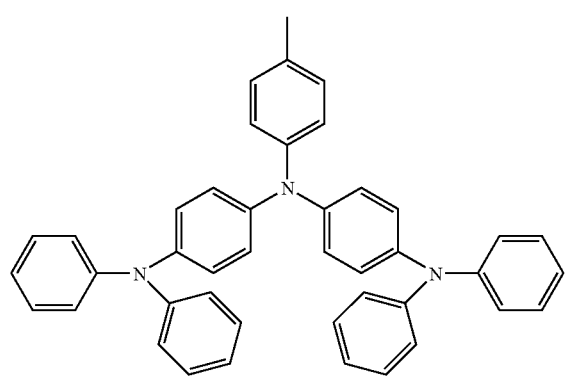

5556 battery, 5561 main body, 5562 voice output portion, 5563 microphone, 5564 display portion, 5565 operation switches, 5566 antenna

BEST MODE FOR CARRYING OUT THE INVENTION

In the present embodiment, a fundamental structure of a light-emitting element using a compound represented by the above general formulas or structure formulas (6) to (15) is described with reference to FIG. 1. The structure of the element shown in the implement of the present invention is a structure in which a hole injecting layer, a hole transporting layer, a light-emitting layer, and an electron transporting layer are provided between a cathode and an anode. However, the present invention is not limited to this, and various light-emitting element structures, for example, structures such as an anode/a hole injecting layer/a light-emitting layer/an electron transporting layer/a cathode, an anode/a hole injecting layer/a hole transporting layer/a light-emitting layer/an electron transporting layer/an electron injecting layer/a cathode, an anode/a hole injecting layer/a hole transporting layer/a light-emitting layer/a hole blocking layer/an electron transporting layer/a cathode, and an anode/a hole injecting layer/ a hole transporting layer/a light-emitting layer/a hole blocking layer/an electron transporting layer/an electron injecting layer/a cathode, may be employed. In these light-emitting elements, the compound can be used for the hole injecting layer, the hole transporting layer, or the light-emitting layer.

Figure 1:
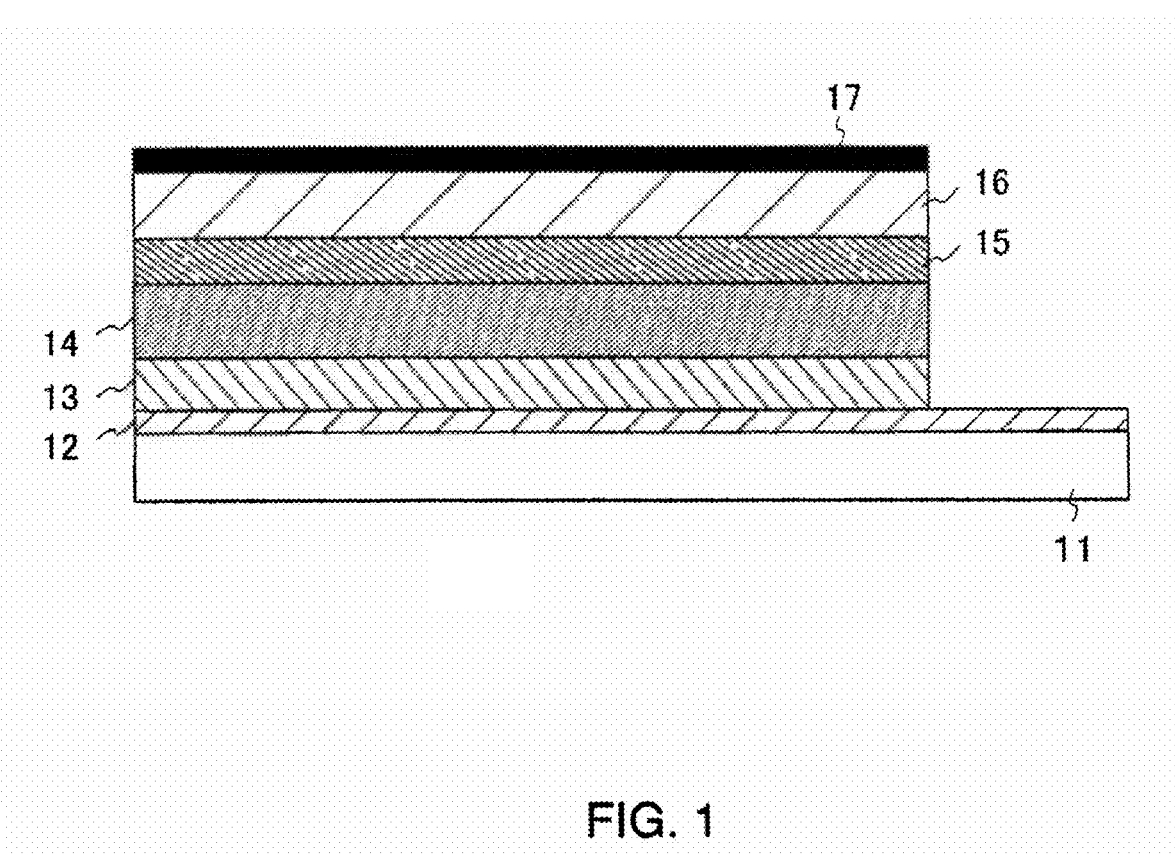
FIG. 1 is a diagram for describing a light-emitting element using a polymer according to the present invention.

In FIG. 1, reference numeral 11 denotes a substrate, supporting a light-emitting element, which can comprise glass, quarts, transparent plastics, or the like. Reference numeral 12 denotes an anode, for which it is preferable to use a metal, an alloy, an electrically conductive compound, a mixture thereof, and the like, which have a large work function (a work function of 4.0 eV or more). As a specific example of the anode material, it is possible to use gold (Au), platinum (Pt), nickel (Ni), tungsten (W), chromium (Cr), molybdenum (Mo), iron (Fe), cobalt (Co), copper (Cu), palladium (Pd) or a nitride of a metal material (TiN), in addition to ITO or IZO (indium zinc oxide) in which indium oxide is mixed with zinc oxide (ZnO) at 2 to 20%.

Reference numeral 13 denotes a hole injecting material, for which a material proposed by the present invention, that is, a material represented by the general formulas or structure formulas (6) to (15) is used. Reference numeral 14 denotes a hole transporting material, for which a known material can be used. As typical examples, there are aromatic amine compounds, which include, for example, 4,4'-bis[N-(1-naphthyl)-N-phenyl-amino]-biphenyl (hereinafter, referred to as α-NPD) and starburst aromatic amine compounds such as 4,4',4"-tris(N,N-diphenyl-amino)-triphenylamine (hereinafter, referred to as TDATA) and 4,4',4"-tris[N-(3-methylphenyl)-N-phenyl-amino]-triphenylamine (hereinafter, referred to as MTDATA). Reference numeral 15 denotes a light-emitting layer, which may be known, for which various fluorescent dyes are efficient in addition to metal complexes such as tris (8-quinolinolato) aluminum (hereinafter, referred to as $Alq_3$), tris (4-methyl-8-quinolinolato)aluminum (hereinafter, referred to as $Almq_3$), bis(10-hydroxybenzo [η]-quinolinato) beryllium (hereinafter, referred to as $BeBq_2$), bis(2-methyl-8-quinolinolato)-(4-hydroxy-biphenylyl)-aluminum (hereinafter, referred to as BAlq), bis[2-(2-hydroxyphenyl)-benzoxazolato]zinc (hereinafter, referred to as $Zn(BOX)_2$), and bis[2-(2-hydroxyphenyl-benzothiazolato)zinc (hereinafter, referred to as $Zn(BTZ)_2$). Reference numeral 16 denotes an electron transporting layer, for which a known material can be used. Specifically, as typified by a tris (8-quinolinolato) aluminum complex (hereinafter, referred to as $Alq_3$), a metal complex that has a quinoline skeleton or a benzoquinoline skeleton and a mixed ligand complex thereof are preferred. In addition to the metal complexes, oxadiazole derivatives such as 2-(4-biphenylyl)-5-(4-tert-butylphenyl)-1,3,4-oxadiazole (hereinafter, referred to as PBD) and 1,3-bis[5-(p-tert-butylphenyl)-1,3,4-oxadiazole-2-yl]benzene (hereinafter, referred to as OXD-7), triazole derivatives such as 3-(4-tert-butylphenyl)-4-phenyl-5-(4-biphenylyl)-1,2,4-triazole (hereinafter, referred to as TAZ) and 3-(4-tert-butylphenyl)-4-(4-ethylphenyl)-5-(4-biphenylyl)-1,2,4-triazole (hereinafter, referred to as p-EtTAZ), and phenanthroline derivatives such as bathophenanthroline (hereinafter, referred to as BPhen) and bathocuproin (hereinafter, referred to as BCP) can be used.

In the element shown in FIG. 1, a cathode 17 is formed on these respective functional layers. As the cathode, it is preferable to use a metal, an alloy, an electrically conductive compound, a mixture thereof, and the like, which have a small work function. Specifically, in addition to representative elements belonging to Group 1 or 2, that is, alkali metals such as Li and Cs, alkali earth metals such as Mg, Ca, and Sr, and alloys (Mg:Ag, Al:Li) and compounds (LiF, CsF, $CaF_2$) including these, transition metals including rare-earth metals can be used to form the cathode. However, the cathode can also be formed by a lamination layer of metals (including alloys) such as Al, Ag, and ITO.

The above-mentioned anode materials and cathode materials are formed by a method such as evaporation or sputtering.

By conducting between the electrodes of the light-emitting element shown in FIG. 1, an electron injected from a cathode and a hole injected from an anode are recombined to emit light.

EXAMPLE 1

Synthesis Example 1

In the present synthesis example, synthesis of a compound shown by the structure formula (5), 2-ethenyl-3,4-ethylenedioxythiophene, will be described. The synthesis scheme (a) is shown as follows.

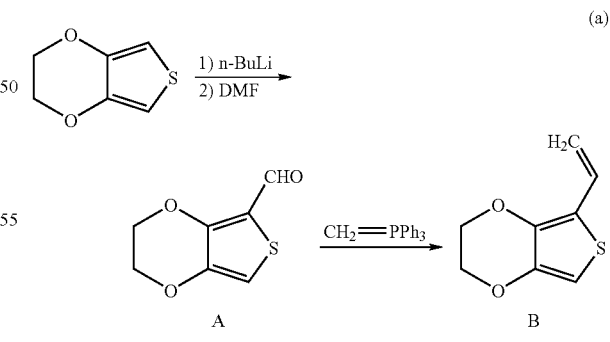

Under a nitrogen atmosphere, a 1.58 N hexane solution of n-butyllithium (158 mL, 0.1 mol) was dropped at −78° C. in a dried tetrahydrofran (130 mL) solution of 3,4-ethylenedioxythiophene (13.8 g, 0.1 mol). After the dropping, stirring was performed at −78° C. for 45 minutes. After adding dried DMF (7.3 g, 0.1 mol) to this suspension, the reaction mixture was heated at 45° C. for 2 hours. About 100 mL of 1 N HCl was added to the reaction mixture, and stirring was continued further for 10 minutes. The reaction solution was extracted with ether, and the ether was removed. By recrystallizing the residue with hexane, 2-formyl-3,4-ethylenedioxythiophene (a compound A in the synthesis scheme (a), 13.21 g, yield: 84%) was obtained.

Under a nitrogen atmosphere, a 1.58 N hexane solution of n-butyllithium (49 mL, 78 mmol) was dropped at −40° C. in a dried THF solution of a methyltriphenylphosphonium iodide salt (78 mmol). After the dropping, and then cooling to −78° C., a dried THF solution (70 mL) of 2-formyl-3,4-ethylenedioxythiophene (the compound A in the synthesis scheme (a)) was added to this. After that, the reaction mixture was brought back to a room temperature, and stirring was performed for 24 hours. The reaction solution was extracted with ether, and the ether was removed. By purifying the residue by silica-gel chromatography (developing solvent: hexane/ethyl acetate), 2-ethenyl-3,4-ethylenedioxythiophene represented by the structure formula (5) (a compound B in the synthesis scheme (a), 6.93 g, yield: 58%) was obtained. Here is NMR data of the compound B. $^1$H NMR (300 MHz, CDCl$_3$) δ 6.70 (dd, J=11, 18 Hz, 1H), 6.18 (s, 1H), 5.48 (q, J=18 Hz, 1H), 5.06 (d, J=11 Hz 1H), 4.18-4.25 (m, 4H)

Synthesis Example 2

In the present synthesis example, an example of homopolymerization of 2-ethenyl-3,4-ethylenedioxythiophene represented by the structure formula (5) will be described. The synthesis scheme (b) is shown below.

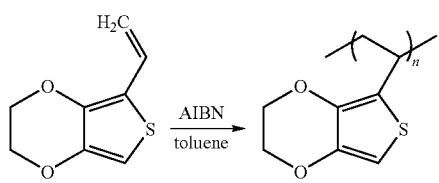
(b)

Under nitrogen, 2-ethenyl-3,4-ethylenedioxythiophene (1.3 g) was dissolved in 1 mL of toluene, and azobisisobutyronitrile (32.8 mg) dissolved in 1 mL of toluene was added. The reaction solution was left at 60° C. for 24 hours. By putting the reaction solution in excess ethanol, and filtering and drying generated precipitation, a corresponding polymer, poly(2-ethenyl-3,4-ethylenedioxythiophene), was obtained. Yield: 50 mg (yield: 36%). The decomposition temperature and glass transition temperature of this compound under a nitrogen atmosphere were 340° C. and 158° C., respectively. The ionization potential was 5.60 eV.

Synthesis Example 3

In the present synthesis example, an example of copolymerization of 2-ethenyl-3,4-ethylenedioxythiophene represented by the structure formula (5) and N-vinylcarbazole in a solution will be described. The synthesis scheme (c) is shown below.

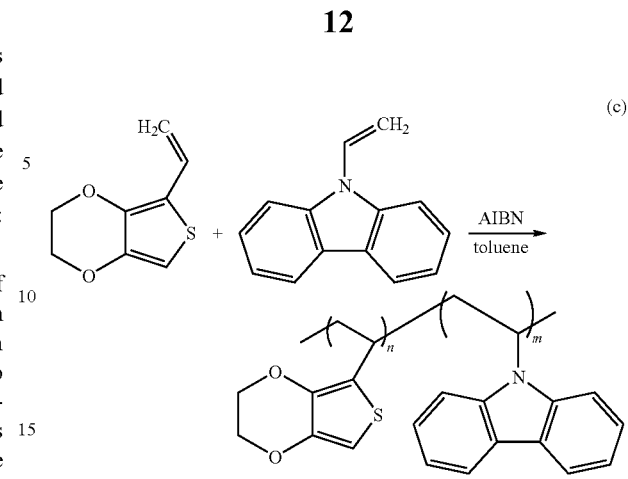
(c)

Under nitrogen, 2-ethenyl-3,4-ethylenedioxythiophene (0.4 mmol) and N-vinylcarbazole (3.6 mmol) were dissolved in 1 mL of toluene, and azobisisobutyronitrile (0.2 mmol) dissolved in 1 mL of toluene was added. The reaction solution was left at 60° C. for 24 hours. By putting the reaction solution in excess methanol, and filtering and drying generated precipitation, a polymer shown by the general formula (15), poly (2-ethenyl-3,4-ethylenedioxythiophene-co-N-vinylcarbazole), was obtained. Yield: 79 mg (yield: 32%). The 5% weight loss temperature of this copolymer under a nitrogen atmosphere was 190° C. In addition, in a differential scanning calorimetry measurement (DSC measurement), no grass transition temperature was shown at this temperature or less.

Synthesis Example 4

In the present synthesis example, an example of bulk copolymerization of 2-ethenyl-3,4-ethylenedioxythiophene represented by the structure formula (5) and N-vinylcarbazole will be described. The synthesis scheme (d) is shown below.

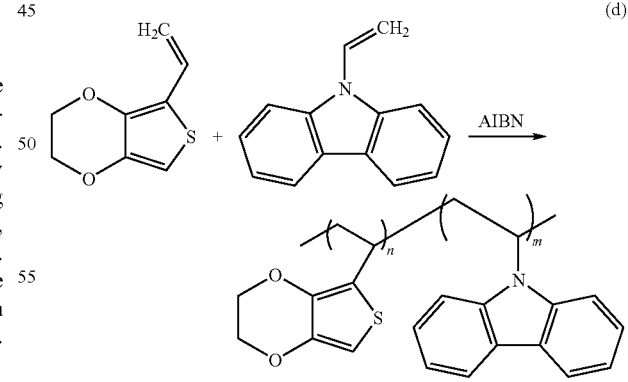
(d)

Under nitrogen, azobisisobutyronitrile (0.29 mmol) was added to 2-ethenyl-3,4-ethylenedioxythiophene (0.57 mmol) and N-vinylcarbazole (5.24 mmol) to react at 80° C. for 48 hours. By reprecipitating a generated polymer with methanol, a copolymer shown by the general formula (15) was isolated. Yield: 230 mg (yield: 21%).

EXAMPLE 2

An example of manufacturing a light-emitting element using the copolymer obtained in the above-described synthesis example as a hole injecting layer, and characteristics of the element will be shown.

Onto ITO deposited on a glass substrate, a solution in which the copolymer represented by the structure formula (15) was dissolved in chloroform was applied by spin coating to form a copolymer film as a hole injecting layer. Thereon, N,N'-di(naphthalene-1-yl)-N, N'-diphenylbenzidene (hereinafter, referred to as NPB) that is a hole transporting material was deposited by vacuum deposition as a hole transporting layer. Further, a tris(8-quinolinolato)aluminum complex (hereinafter, referred to as Alq) was vacuum-deposited as a light-emitting layer. Further, Al and Li were co-deposited to form a cathode.

Figure 4:
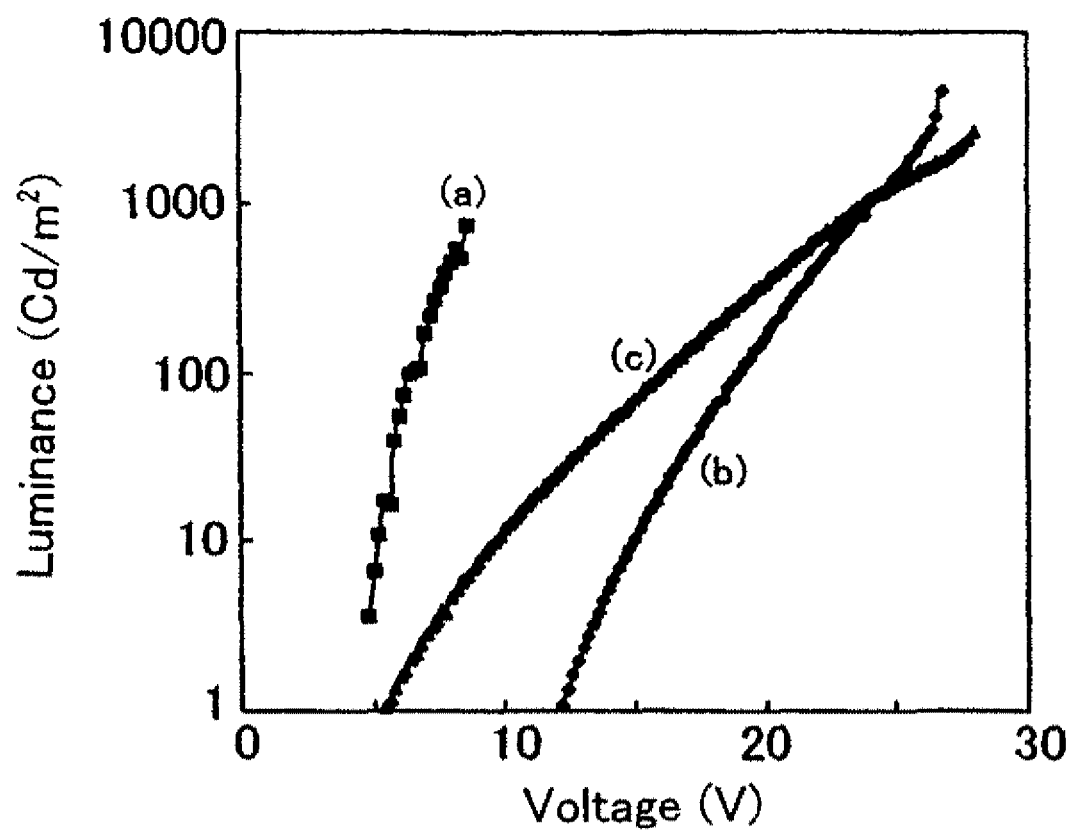
FIG. 4 is a diagram for describing luminance-voltage characteristics of a light-emitting element according to the present invention.

FIG. 4 shows voltage (V)-luminance ($Cd/m^2$) characteristics of the light-emitting element manufactured as described above. As shown by (a) in FIG. 4, the light-emitting element according to the present invention started to emit light from 4.8 V, and green luminescence was obtained with luminous efficiency 4.0 cd/A. However, in the case where poly(N-vinylcarbazole) was used as a polymer hole injecting material and NPB was used as a hole transporting material, the light-emission starting voltage is 12.0 V as shown by (b) in FIG. 4, so that the light-emission starting voltage of the copolymer represented by the structure formula (15) according to the present invention is found to be much lower. This indicates that the structure shown by the structure formula (15) is useful. In the case where copper phthalocyanine that is most often used as a low-molecular hole injecting layer was used as a hole injecting material and NPB was used as a hole transporting material, the light-emission starting voltage is 5.4 V as shown by (c) in FIG. 4. Namely, the hole injecting material according to the present invention was found to show a hole injecting property comparable to that of copper phthalocyanine.

EXAMPLE 3

In the present example, a light-emitting device that has a light-emitting element according to the present invention in a pixel portion will be described with reference to FIG. 2. FIG. 2(A) is a top view showing the light-emitting device and FIG. 2(B) is a cross-sectional view taken along line A-A' in FIG. 2(A). Reference numeral 401 indicated by a dotted line denotes a driver circuit portion (a source side driver circuit), reference numeral 402 denotes a pixel portion, and reference numeral 403 denotes a driver circuit portion (a gate side driver circuit). In addition, reference numerals 404 and 405 denote a sealing substrate and a sealing material, respectively. The inside surrounded by the sealing material 405 is a space 407.

A wiring 408 for transmitting signals to be input to the source side driver circuit 401 and the gate side driver circuit 403, receives signals such as a video signal, a clock signal, a start signal, and a reset signal from FPC (Flexible Printed Circuit) 409 that serves as an external input terminal. Though only the FPC is shown in the figure here, a printed wiring board (PWB) may be attached to this FPC. The light-emitting device in this example includes not only a light-emitting device body but also a state where an FPC or a PWB is attached thereto.

Next, the sectional structure will be explained with reference to FIG. 2(B). The driver circuits and the pixel portion are formed over an element substrate 410. Here, the source side driver circuit 401 as the driver circuit portion and the pixel portion 402 are shown.

In the source side driver circuit 401, a CMOS circuit which is a combination of an n-channel TFt 423 and a p-channel TFT 424 is formed. The TFTs forming the driver circuit may be formed of a known CMOS circuit, PMOS circuit, or NMOS circuit. Although the present embodiment shows a driver integrated type in which a driver circuit is formed over a substrate, which is not always necessary, the driver circuit can be formed not over the substrate but outside the substrate.

The pixel portion 402 has a plurality of pixels, each including a switching TFT 411, a current controlling TFT 412, and a first electrode 413 electrically connected to a drain thereof. In addition, an insulator 414 is formed to cover an edge of the first electrode 413. Here, a positive photosensitive acrylic resin film is used to form the insulator 414.

Besides, in order to obtain a favorable coverage, the insulator 414 is made to have a curved surface with a curvature in its top portion or bottom potion. For example, in the case of using positive photosensitive acrylic as a material for the insulator 414, it is preferable that only a top portion of the insulator 414 has a curved surface with a curvature radius (0.2 µm to 3 µm). In addition, both a negative type material that becomes insoluble in an etchant by light and a positive type material that becomes soluble in an etchant by light can be used as the insulator 414.

On the first electrode 413, a layer 416 including a luminescent material and a second electrode 417 are formed. Here, as a material to be used for the first electrode 413 that functions as an anode, it is preferable to use a material that has a large work function. For example, in addition to single layers such as an ITO (indium tin oxide) film, an indium zinc oxide (IZO) film, a titanium nitride film, a chromium film, a tungsten film, a Zn film, and a Pt film, a laminate of titanium nitride and a film including aluminum as its main component, a three-layer structure of a titanium nitride film, a film including aluminum as its main component, and a titanium nitride film, and the like can be used. When a laminated structure is employed, the wiring has a lower resistance, favorable ohmic contact can be taken, and it is possible to function as an anode.

The layer 416 including the luminescent material is formed by evaporation that uses an evaporation mask or by inkjet. For a portion of the layer 416 including the luminescent material, an organic compound according to the present invention is used. In addition, as materials that can be used for the layer 416 including the luminescent material, a low molecular weight material and a high molecular weight material may be used. Moreover, as a material to be used for the layer 416 including the luminescent material, it is often the case that an organic material is used for a single layer or laminate. However, the present invention includes a structure in which an inorganic compound is used for a part of a film including an organic compound.

In the case where it is desired to obtain a multicolor display image, a layer including an organic compound according to the present invention as a luminescent material may be formed separately depending on each different emission color by using a mask or a partition layer. In this case, a layer including a luminescent material for displaying each emission color may have a different laminated structure.

In addition, as a material to be used for the second electrode (cathode) 417 formed on the layer 416 including the luminescent material, a material that has a small work function (Al, Ag, Li, or Ca; an alloy thereof such as MgAg, Mgln, Al-Li, $CaF_2$, or CaN) may be used. In the case of transmitting light generated in the layer 416 including the luminescent material through the second electrode 417, it is preferable to use a laminate of a metal thin film that has a thinned film thickness and a transparent conductive film (such as ITO (indium tin oxide), an alloy of indium oxide and zinc oxide (In₂O₃—ZnO), or zinc oxide (ZnO)) as the second electrode (cathode) 417.

Further, the sealing substrate 404 and the element substrate 410 are bonded with the sealing material 405 to have a structure where a light-emitting element 418 is provided in the space 407 surrounded by the element substrate 410, the sealing substrate 404, and the sealing material 405. The space 407 also includes a structure of filling with the sealing material 405 in addition to a case of filling with an inert gas (such as nitrogen or argon).

It is preferable to use an epoxy resin for the sealing material 405. In addition, it is desirable to use a material that allows permeation of moisture or oxygen as little as possible. Further, as a material to be used for the sealing substrate 404, a plastic substrate including FRP (Fiberglass-Reinforced Plastics), PVF (polyvinylfluoride), Mylar, polyester, or acrylic can be used besides a glass substrate and a quarts substrate.

In the light-emitting device that has the light-emitting element according to the present invention as described above, a defect due to water, a strongly acidic material, or the like is suppressed, so that favorable display images can be obtained.

EXAMPLE 4

In the present example, electronic devices to which the present invention is applied will be described with reference to FIG. 3. By applying the present invention, for example, in electronic devices as shown below, favorable display images can be obtained, where a defect due to water, a strongly acidic material, or the like is suppressed.

Figure 3A:
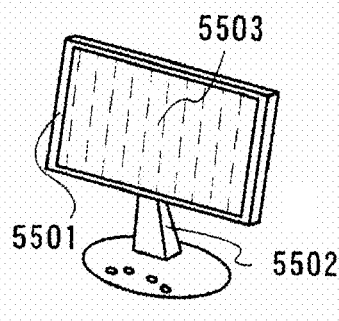
FIG. 3 is a diagram for describing electronic devices to which the present invention is applied.

FIG. 3(A) is a display device, which includes a frame body 5501, a support 5502, and a display portion 5503. A display device can be completed by incorporating the light-emitting device shown in Example 3 in the display device.

Figure 3B:
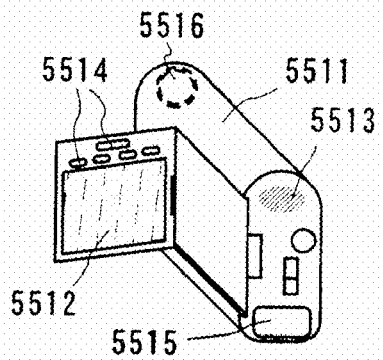

FIG. 3(B) is a video camera, which includes a main body 5511, a display portion 5512, a voice input 5513, operation switches 5514, a battery 5515, and an image receiving portion 5516. A display device can be completed by incorporating the light-emitting device shown in Example 3 in the video camera.

Figure 3C:
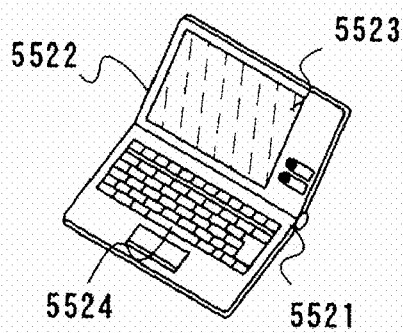

FIG. 3(C) is a laptop personal computer manufactured by applying the present invention, which includes a main body 5521, a frame body 5522, a display portion 5523, and a keyboard 5524. A display device can be completed by incorporating the light-emitting device shown in Example 3 in the laptop personal computer.

Figure 3D:
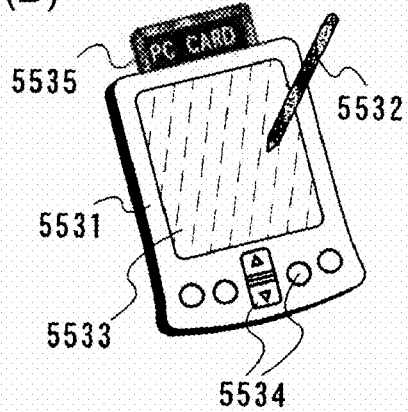

FIG. 3(D) is a personal digital assistance (PDA) manufactured by applying the present invention, which includes a main body 5531 provided with a display portion 5533, an external interface 5535, operation buttons 5534, and the like. As an attachment for operations, a stylus 5532 is provided. A display device can be completed by incorporating the light-emitting device shown in Example 3 in the personal digital assistance (PDA).

Figure 3E:
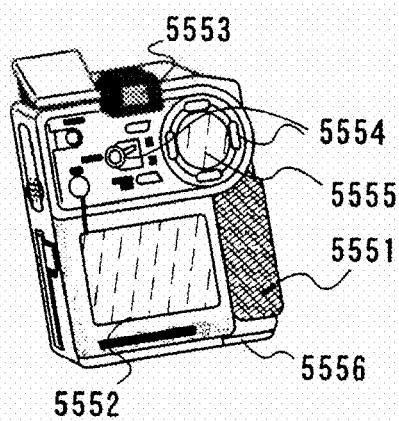

FIG. 3(E) is a digital camera, which includes a main body 5551, a display portion (A) 5552, an eye piece 5553, operation switches 5554, a display portion (B) 5555, and a battery 5556. A display device can be completed by incorporating the light-emitting device shown in Example 3 in the digital camera.

Figure 3F:
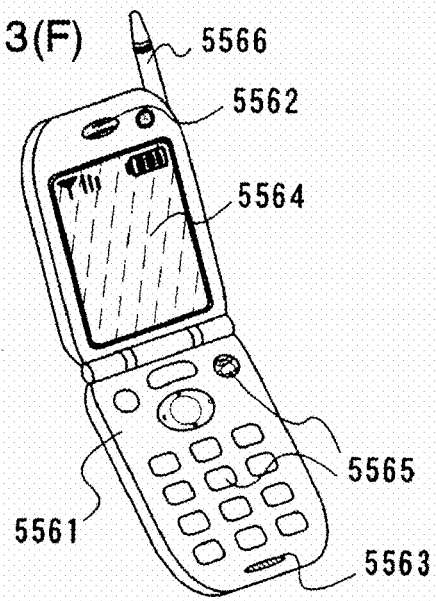

FIG. 3(F) is a cellular phone manufactured by applying the present invention, which includes a main body 5561 provided with a display portion 5564, a voice output portion 5562, a microphone 5563, operation switches 5565, an antenna 5566, and the like. A display device can be completed by incorporating the light-emitting device shown in Example 3 in the cellular phone.

As described above, a light-emitting device obtained by implementing the present invention may be used as display portions of all kinds of electronic devices.

What is claimed is:

1. A polymer represented by a general formula (6)

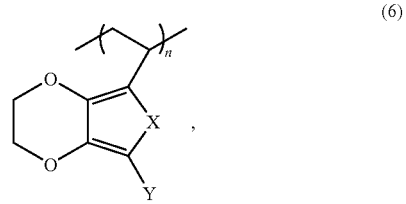

wherein:
X represents any one of an oxygen atom and a sulfur atom;
Y represents any one of a hydrogen atom, an alkyl group, an aryl group, and a silyl group which has an alkyl group or an aryl group; and
n is an integer larger than 1.

2. A polymer represented by a general formula (7)

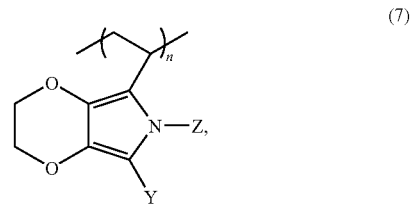

wherein:
Y represents any one of a hydrogen atom, an alkyl group, an aryl group, and a silyl group which has an alkyl group or an aryl group;
Z represents any one of a hydrogen atom, an alkyl group, and an unsubstituted or substituted aryl group; and
n is an integer larger than 1.

3. A polymer represented by a general formula (8)

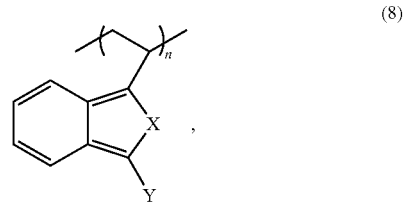

wherein:
X represents any one of an oxygen atom and a sulfur atom;
Y represents any one of a hydrogen atom, an alkyl group, an aryl group, and a silyl group which has an alkyl group or an aryl group; and
n is an integer larger than 1.

4. A polymer represented by a general formula (9)

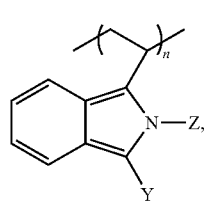

(9)

wherein:
Y represents any one of a hydrogen atom, an alkyl group, an aryl group, and a silyl group which has an alkyl group or an aryl group;
Z represents any one of a hydrogen atom, an alkyl group, and an unsubstituted or substituted aryl group; and
n is an integer larger than 1.

5. The polymer according to claim 1,
wherein X represents a sulfur atom.

6. The polymer according to claim 1,
wherein X represents a hydrogen atom or a substituted or unsubstituted phenyl group.

7. The polymer according to claim 2,
wherein Z represents a substituted or unsubstituted phenyl group.

8. The polymer according to claim 2,
wherein Y represents a hydrogen atom or a substituted or unsubstituted phenyl group.

9. The polymer according to claim 3,
wherein X represents a sulfur atom.

10. The polymer according to claim 3,
wherein Y represents a hydrogen atom or a substituted or unsubstituted phenyl group.

11. The polymer according to claim 4,
wherein Z represents a substituted or unsubstituted phenyl group.

12. The polymer according to claim 4,
wherein Y represents a hydrogen atom or a substituted or unsubstituted phenyl group.

13. A copolymer represented by a general formula (11)

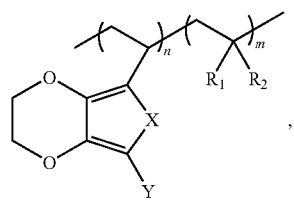

(11)

wherein:
X represents any one of an oxygen atom and a sulfur atom;
Y represents any one of a hydrogen atom, an alkyl group, an aryl group, and a silyl group which has an alkyl group or an aryl group;
$R_1$ represents a hydrogen atom or an alkyl group;
$R_2$ represents any one of an unsubstituted or substituted aryl group, an ester group, a cyano group, an amide group, an alkoxy group, an oxycarbonylalkyl group, and a diarylamino group; and
n and m are individually an integer larger than 1.

14. A copolymer represented by a general formula (12)

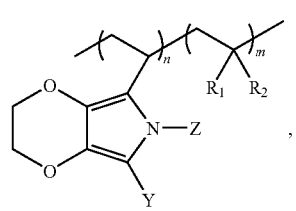

(12)

wherein:
Y represents any one of a hydrogen atom, an alkyl group, an aryl group, and a silyl group which has an alkyl group or an aryl group;
Z represents any one of a hydrogen atom, an alkyl group, and an unsubstituted or substituted aryl group;
$R_1$ represents a hydrogen atom or an alkyl group;
$R_2$ represents any one of an unsubstituted or substituted aryl group, an ester group, a cyano group, an amide group, an alkoxy group, an oxycarbonylalkyl group, and a diarylamino group; and
n and m are individually an integer larger than 1.

15. A copolymer represented by a general formula (13)

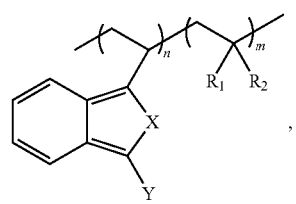

(13)

wherein:
X represents any one of an oxygen atom and a sulfur atom;
Y represents any one of a hydrogen atom, an alkyl group, an aryl group, and a silyl group which has an alkyl group or an aryl group;
Z represents any one of a hydrogen atom, an alkyl group, and an unsubstituted or substituted aryl group;
$R_1$ represents a hydrogen atom or an alkyl group;
$R_2$ represents any one of an unsubstituted or substituted aryl group, an ester group, a cyano group, an amide group, an alkoxy group, an oxycarbonylalkyl group, and a diarylamino group; and
n and m are individually an integer larger than 1.

16. A copolymer represented by a general formula (14)

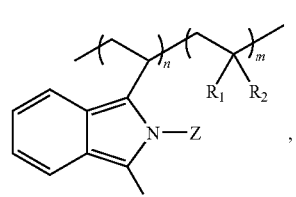

(14)

wherein:
Y represents any one of a hydrogen atom, an alkyl group, an aryl group, and a silyl group which has an alkyl group or an aryl group;

Z represents any one of a hydrogen atom, an alkyl group, and an unsubstituted or substituted aryl group;
$R_1$ represents a hydrogen atom or an alkyl group;
$R_2$ represents any one of an unsubstituted or substituted aryl group, an ester group, a cyano group, an amide group, an alkoxy group, an oxycarbonylalkyl group, and a diarylamino group; and
n and m are individually an integer larger than 1.

17. The copolymer according to claim 13, wherein X represents a sulfur atom.

18. The copolymer according to claim 13, wherein X represents a hydrogen atom or a substituted or unsubstituted phenyl group.

19. The copolymer according to claim 14, wherein Z represents a substituted or unsubstituted phenyl group.

20. The copolymer according to claim 14, wherein Y represents a hydrogen atom or a substituted or unsubstituted phenyl group.

21. The copolymer according to claim 15, wherein X represents a sulfur atom.

22. The copolymer according to claim 15, wherein Y represents a hydrogen atom or a substituted or unsubstituted phenyl group.

23. The copolymer according to claim 16, wherein Z represents a substituted or unsubstituted phenyl group.

24. The copolymer according to claim 16, wherein Y represents a hydrogen atom or a substituted or unsubstituted phenylgroup.

25. A copolymer represented by a structure formula (15)

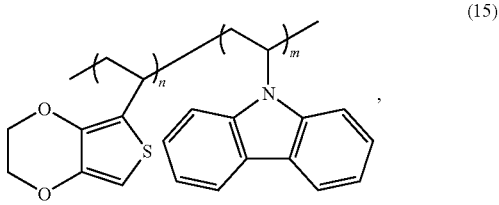

(15)

wherein n and m are individually an integer larger than.

26. A light-emitting element comprising the polymer as in any of claims 1 to 4.

27. An electronic device comprising a light-emitting element which comprises the polymer as in any of claims 1 to 4.

28. A light-emitting element comprising the copolymer as in any of claims 13 to 16.

29. An electronic device comprising a light-emitting element which comprises the copolymer as in any of claims 13 to 16.

* * * * *